(12) United States Patent
Kharrat et al.

(10) Patent No.: US 9,513,210 B2
(45) Date of Patent: Dec. 6, 2016

(54) METHOD FOR MEASURING FRACTIONS OF HYDROCARBON FLUIDS USING OPTICAL SPECTROSCOPY

(75) Inventors: Abdel M. Kharrat, Edmonton (CA); Shahnawaz Hossain Molla, Edmonton (CA); Farshid Mostowfi, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 825 days.

(21) Appl. No.: 13/818,893

(22) PCT Filed: Jul. 22, 2011

(86) PCT No.: PCT/IB2011/053288
§ 371 (c)(1),
(2), (4) Date: Jun. 5, 2013

(87) PCT Pub. No.: WO2012/025845
PCT Pub. Date: Mar. 1, 2012

(65) Prior Publication Data
US 2013/0242288 A1    Sep. 19, 2013

Related U.S. Application Data

(60) Provisional application No. 61/377,354, filed on Aug. 26, 2010.

(51) Int. Cl.
*G01N 21/31* (2006.01)
*G01N 33/28* (2006.01)
*G01N 21/59* (2006.01)

(52) U.S. Cl.
CPC ........ *G01N 21/314* (2013.01); *G01N 33/2835* (2013.01); *G01N 21/5907* (2013.01)

(58) Field of Classification Search
CPC ................................ G01N 21/31; G01J 3/427
See application file for complete search history.

(56) References Cited

U.S. PATENT DOCUMENTS 4,843,247 A * 6/1989 Yamazoe et al. ............. 250/573
2007/0120051 A1   5/2007 DiFoggio et al.

FOREIGN PATENT DOCUMENTS

EP          0551145 A1      7/1993

OTHER PUBLICATIONS

Aske, Narve, Harald Kallevik, and Johan Sjoblom, "Determination of Saturate, Aromatic, Resin and Asphaltenic (SARA) Components in Crude Olls by Means of Infrared and Near-Infrared Spectrscopy," Energy and Fuels 2001, 15, 1304-1312.*

(Continued)

*Primary Examiner* — Kara E Geisel
*Assistant Examiner* — Rebecca C Bryant
(74) *Attorney, Agent, or Firm* — Daniel S. Matthews

(57) ABSTRACT

A method for measuring saturate, aromatic, and resin fractions of a hydrocarbon fluid includes separating maltenes from the hydrocarbon fluid and separating saturate, aromatic, and resin fractions from the maltenes. The method further includes determining an optical density of each of the saturate, aromatic, and resin fractions at a predetermined wavelength and correlating the optical density of each of the saturate, aromatic, and resin fractions to predetermined data to determine each of the saturate, aromatic, and resin fractions.

25 Claims, 3 Drawing Sheets

(56) References Cited

OTHER PUBLICATIONS

Kharrat, Abdel M, Jose Zacharia, V.John CHerian, and ALlwell Anyatonwu, "Issues Comparing SARA Methodologies," Energy and Fuels 2007, 21, 3618-3621.*
Rudzinski, Walter, Tejraj Aminabhavi, Steve Sassman, and Linette Watkins, "Isolation and Characterization of the Saturate and Aromatic Fractions of a Maya Crude Oil," Energy and Fuels 2000, 14, 839-844, Jun. 17, 2000.*
International Search Report for PCT Application Serial No. PCT/IB2011/053288 dated Nov. 17, 2011.
Bacaud, "Petroleum Residues, Characterization of" in "Encyclopedia of Analytical Chemistry", Sep. 15, 2006, John Wiley & Sons, Ltd., Chichester, UK, XP55011688, ISBN: 978-0-47-002731-8.
Bouquet, et al., "Determination of asphaltene content in petroleum products for concentrations below 20000 ppm down to 150 ppm," Fuel, IPC Science and Technology Press, Guildford, GB, vol. 64, No. 11, Nov. 1, 1985, pp. 1625-1627, XP025457790, ISSN: 0016-2361.
Fahim et al., "Fundamentals of Petroleum Refining", Dec. 14, 2009, p. 29, Elsevier Science, ISBN: 9780444527851.
Canadian Examination Report for corresponding Canadian Application No. 2,809,419 dated Jul. 17, 2015, 3 pages.

\* cited by examiner

METHOD FOR MEASURING FRACTIONS OF HYDROCARBON FLUIDS USING OPTICAL SPECTROSCOPY

This application claims priority from U.S. Provisional Application 61/377,354, filed on Aug. 26, 2010, which is incorporated herein by reference.

BACKGROUND OF THE INVENTION

1. Field of the Invention

The present invention relates to a method for measuring fractions of hydrocarbon fluids using optical spectroscopy.

2. Description of Related Art

It is often desirable for many reasons to characterize the compositions of hydrocarbon fluids, such as crude oil. For example, the behavior of a hydrocarbon fluid depends, at least in part, on the composition of the hydrocarbon fluid. Proper reservoir management utilizes data concerning pressure and temperature of the reservoir along with the composition of the hydrocarbon reservoir fluids. Moreover, the mixing of different hydrocarbon fluids during transportation and/or storage of hydrocarbon fluids can cause perturbation of the fluids system. For example, the presence of incompatible fluids can result in precipitation of solids and the deposition of such solids within transportation and/or storage equipment.

One of the more common methods used to characterize the compositions of hydrocarbon fluids involves the separation of such fluids into four fractions, i.e., saturates, aromatics, resins, and asphaltenes, then weighing each fraction to determine the composition of the hydrocarbon fluid. Such weight-based measurements are cumbersome and costly, as substantial quantities of solvents, adsorbent, and oil are required for testing accuracy.

There are methods for characterizing the compositions of hydrocarbon fluids that are well known in the art, however, considerable shortcomings remain.

BRIEF SUMMARY OF THE INVENTION

In one aspect, the present invention provides a method for measuring saturate, aromatic, and resin fractions of a hydrocarbon fluid. The method comprises separating maltenes from the hydrocarbon fluid and separating saturate, aromatic, and resin fractions from the maltenes. The method further includes determining an optical density of each of the saturate, aromatic, and resin fractions and correlating the optical density of each of the saturate, aromatic, and resin fractions to predetermined data to determine each of the saturate, aromatic, and resin fractions.

The present invention provides significant advantages, including, but not limited to, providing a way to determine the saturate, aromatic, and resin fractions of a hydrocarbon fluid by using much smaller portions of the fractions than those required in conventional methods.

Additional objectives, features and advantages will be apparent in the written description which follows.

BRIEF DESCRIPTION OF THE DRAWINGS

The features of the invention are set forth in the appended claims. However, the invention itself, as well as a preferred mode of use, and further objectives and advantages thereof, will best be understood by reference to the following detailed description when read in conjunction with the accompanying drawings, in which the leftmost significant digit(s) in the reference numbers denote(s) the first figure in which the respective reference numbers appear, wherein:

Figure 1:
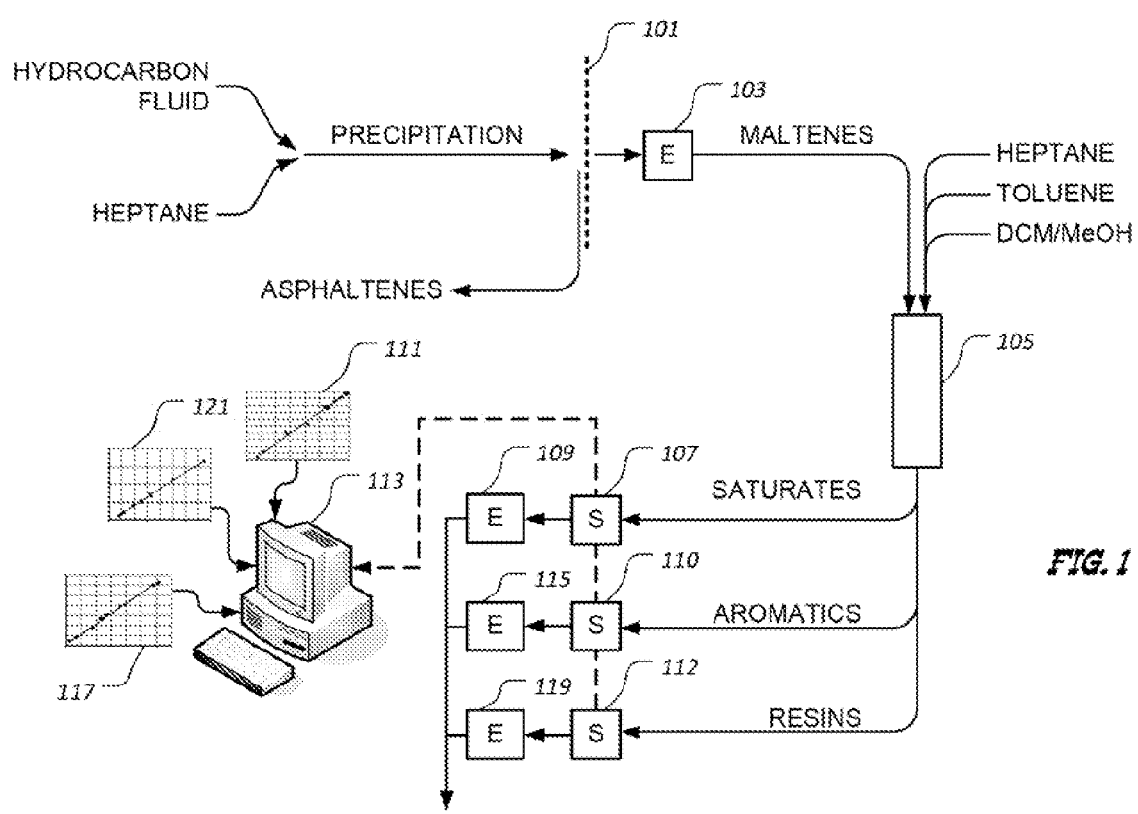
FIG. 1 is a stylized, graphical representation of an illustrative embodiment of a method for measuring saturate, aromatic, and resin fractions of a hydrocarbon fluid.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The present invention provides a new method for measuring saturate, aromatic, and resin fractions of hydrocarbon fluids using optical spectroscopy. Asphaltenes are removed from the hydrocarbon fluid, leaving the remaining maltenes. Each of the saturate, aromatic, and resin constituents are separated from the maltenes. The optical density of each constituent is measured using optical spectroscopy. The optical density is then compared to predetermined data to determine the fraction of the constituent in the hydrocarbon fluid.

FIG. 1 provides a stylized, graphical representation of an illustrative method for measuring saturate, aromatic, and resin fractions of a hydrocarbon fluid, such as crude oil. The hydrocarbon fluid to be tested or measured is titrated with heptane, causing the asphaltenes of the hydrocarbon fluid to be precipitated. The fluid is then passed through a filter 101 to remove the asphaltenes. The filtered fluid is introduced into an evaporator 103, such as a rotary evaporator, to remove the heptane from the mixture, leaving maltenes. A known mass of maltenes, which may be between 100 and 400 mg, is then introduced into an activated alumina packed bed 105, wherein the maltenes are adsorbed onto the surface of the activated alumina. Alternatively, silica or another suitable adsorbent material may be used in packed bed 105. Heptane is then flushed through packed bed 105, causing the saturates to be released from the activated alumina. The saturates are then collected and introduced into a spectrometer 107, which may have a path length of about 10 mm, wherein the optical density of the saturates is measured at a predetermined wavelength. Although not essential for proper functioning of the invention, the optical density of the saturates may be measured at both a shorter wavelength and a longer wavelength and the optical density at the longer wavelength may be subtracted from the optical density at the shorter wavelength to compensate or correct for errors due to the baseline shift of spectrometer 107. In one embodiment, the optical density of the saturates is measured at about 285 nanometers and at about 800 nanometers, wherein the optical density of the saturates at about 800 nanometers is subtracted from the optical density of the saturates at about 285 nanometers. The measured optical density, or the resulting differential optical density normalized based on the injected mass of maltenes, is then compared to correlation data 111 to determine the fraction of saturates in the hydrocarbon fluid. In one embodiment, correlation data 111 is resident in the memory of a computer 113, which is operated to perform the correlation. Finally, the saturates may be introduced into an evaporator 109, such as a rotary evaporator, to remove the heptane from the heptane-saturate mixture.

Toluene is then flushed through packed bed 105, causing the aromatics to be released from the activated alumina. The aromatics are then collected and introduced into spectrometer 110, which may have a path length of about 10 mm, wherein the optical density of the aromatics is measured at a predetermined wavelength. Although not essential for proper functioning of the invention, the optical density of the aromatics may be measured at both a shorter wavelength and a longer wavelength. As described herein concerning the saturates, the optical density of the aromatics at the longer wavelength may be subtracted from the optical density of the aromatics at the shorter wavelength to compensate or correct for errors due to the baseline shift of spectrometer 110. In one embodiment, the optical density of the aromatics is measured at about 470 nanometers and at about 800 nanometers, wherein the optical density of the aromatics at about 800 nanometers is subtracted from the optical density of the aromatics at about 470 nanometers. The measured optical density, or the resulting differential optical density normalized based on the injected mass of maltenes, is then compared to correlation data 117 to determine the fraction of aromatics in the hydrocarbon fluid. In one embodiment, correlation data 117 is resident in the memory of computer 113, which is operated to perform the correlation. Finally, the aromatics may be introduced into evaporator 115, such as a rotary evaporator, to remove the toluene from the toluene-aromatic mixture.

Still referring to FIG. 1, dichloromethane/methanol (DCM/MeOH) is next flushed through packed bed 105, causing the resins to be released from the activated alumina. The resins are then collected and introduced into spectrometer 112, which may have a path length of about 10 mm, wherein the optical density of the resins is measured at a predetermined wavelength. Although not essential for proper functioning of the invention, the optical density of the resins may be measured at both a shorter wavelength and a longer wavelength. As described herein concerning the saturates, the optical density of the resins at the longer wavelength may be subtracted from the optical density of the resins at the shorter wavelength to compensate or correct for errors due to the baseline shift of spectrometer 112. In one embodiment, the optical density of the resins is measured at about 600 nanometers and at about 800 nanometers, wherein the optical density of the resins at about 800 nanometers is subtracted from the optical density of the resins at about 600 nanometers. The measured optical density, or the resulting differential optical density normalized based on the injected mass of maltenes, is then compared to correlation data 121 to determine the fraction of resins in the hydrocarbon fluid. In one embodiment, correlation data 121 is resident in the memory of computer 113, which is operated to perform the correlation. Finally, the resins may be introduced into evaporator 119, such as a rotary evaporator, to remove the DCM/MeOH from the DCM/MeOH-resin mixture.

It should be noted that, while the evaporators depicted in FIG. 1 are provided with different reference numbers, i.e., evaporators 103, 109, 115, and 119, the present invention contemplates using a single evaporator rather than a plurality of evaporators. It should also be noted that the scope of the present invention encompasses the use of a single spectrometer for measuring the optical densities of the maltenes constituents, rather than a plurality of spectrometers 107, 110, and 112, as depicted in FIG. 1. As only small quantities of the saturate, aromatic, and resin fractions are needed to determine the optical densities thereof, the present method is less cumbersome and less costly than conventional methods.

Figure 2:
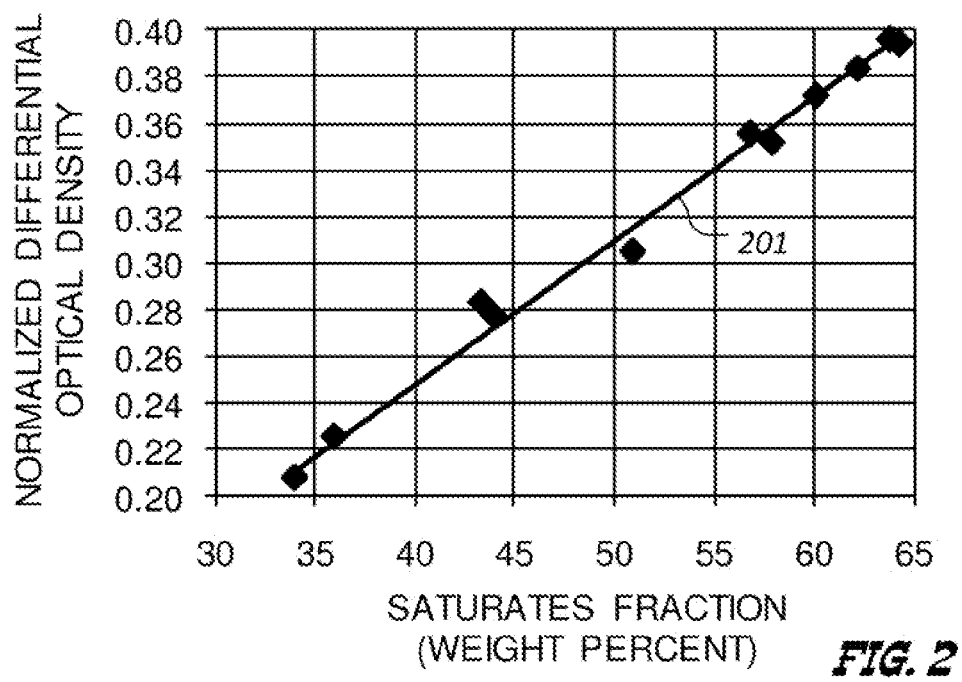
FIGS. 2-4 are graphical representations of exemplary correlations between optical density and the saturate, aromatic, and resin fractions, respectively, of a plurality of hydrocarbon fluids.
Figure 3:
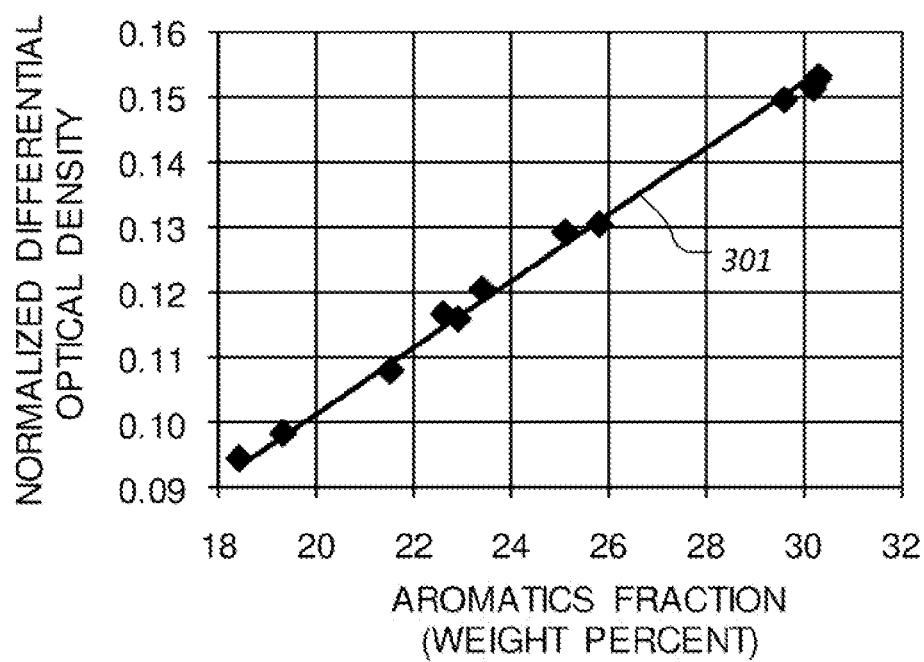
Figure 4:
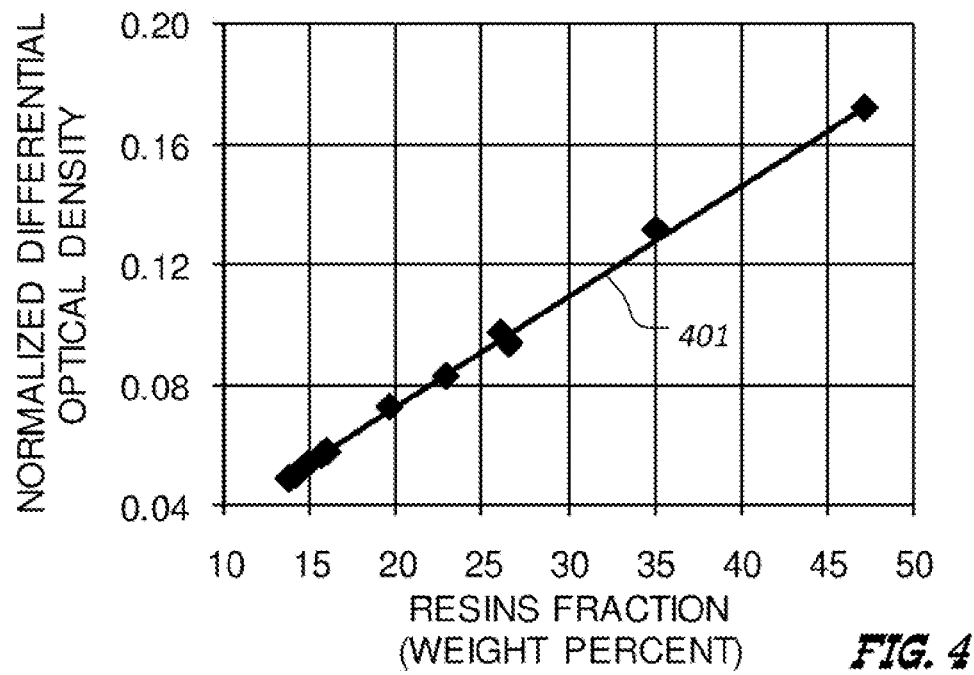

FIGS. 2-4 depict exemplary correlations between normalized differential optical density at two predetermined wavelengths and the saturate, aromatic, and resin fractions, respectively, of a plurality of hydrocarbon fluids. Note that the normalized differential optical density, as the term is used herein, is the result when the optical density of the fraction measured at a longer wavelength is subtracted from the optical density of the fraction measured at a shorter wavelength. For example, the normalized differential optical densities shown in FIG. 2 are the optical densities that resulted from the subtraction of optical densities measured at about 800 nanometers from the optical densities measured at about 285 nanometers. Each of FIGS. 2-4 represent data for a variety of dead hydrocarbon fluids, including, for example, crude oils from the Gulf of Mexico, California, offshore Canada, and the oil sands of Alberta, Canada. To develop the exemplary data shown in FIGS. 2-5, a conventional, weight-based process was used to determine the mass of each constituent in each of the hydrocarbon fluids. Additionally, the differential optical density of each constituent in each of the hydrocarbon fluids was determined. Data points shown in FIGS. 2-4 represent the results of these weight-based and optical-based measurements. Despite the wide variety of types of hydrocarbon fluids measured and fraction content, the data show a high degree of linearity, as represented by lines 201, 301, and 401 of FIGS. 2, 3, and 4, respectively. The data represented in FIGS. 2-4 correspond to correlation data 111, 117, and 121, respectively, depicted in FIG. 1 and used in the method described herein.

Figure 5:
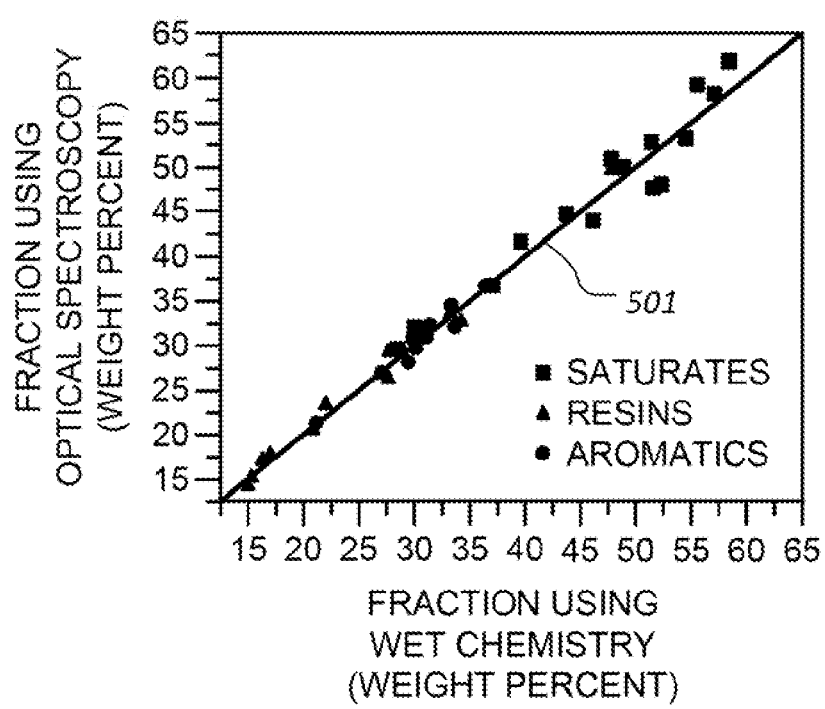
FIG. 5 is a graphical representation illustrating the accuracy of the data of FIGS. 2-4.

To assess the accuracy of the method described herein concerning FIG. 1, the data provided in FIGS. 2-4 are combined and shown in FIG. 5. A line 501 represents a theoretically-perfect correlation between the constituent fraction, as measured using the optical method of FIG. 1, and a conventional, weight-based wet chemistry measurement technique. As can be seen in FIG. 5, the data of FIGS. 2-4 conform well to line 501. In this particular assessment, the deviation of any data point from line 501 does not exceed ten percent.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. The particular embodiments disclosed above may be altered or modified within the scope of the invention. Accordingly, the protection sought herein is as set forth in the claims below. Although the present invention is shown in a limited number of forms, it is not limited to just these forms, but is amenable to various changes and modifications and may be used to evaluate a variety of hydrocarbon fluids.

What is claimed is:

1. A method for measuring saturate, aromatic, and resin fractions of a hydrocarbon fluid, comprising:
separating maltenes from the hydrocarbon fluid;
separating saturate, aromatic, and resin fractions from the maltenes by:
introducing the maltenes to a packed bed;
flushing the packed bed with heptane to separate the saturate fraction from the maltenes;
flushing the packed bed with toluene to separate the aromatic fraction from the maltenes; and
flushing the packed bed with dichloromethane/methanol to separate the resin fraction from the maltenes;
spectroscopically determining an optical density of each of the saturate, aromatic, and resin fractions at a predetermined wavelength; and
correlating the optical density of each of the saturate, aromatic, and resin fractions to predetermined data to determine each of the saturate, aromatic, and resin fractions.

2. The method of claim 1, wherein the optical density of each of the saturate, aromatic, and resin fractions is a differential optical density at two predetermined wavelengths.

3. The method of claim 2, wherein the differential optical density is normalized.

4. The method of claim 1, wherein separating maltenes from the hydrocarbon fluid is accomplished by titrating the hydrocarbon fluid with heptane.

5. The method of claim 4, further comprising removing the heptane from the maltenes.

6. The method of claim 1, wherein the packed bed comprises activated alumina.

7. The method of claim 1, further comprising:
removing the heptane from the saturate fraction;
removing the toluene from the aromatic fraction; and
removing the dichloromethane/methanol from the resin fraction.

8. The method of claim 2, wherein determining the differential optical density of the saturate fraction is accomplished by:
measuring an optical density of the saturate fraction at a shorter wavelength and at a longer wavelength; and
subtracting the optical density of the saturate fraction at the longer wavelength from the optical density of the saturate fraction at the shorter wavelength to produce the differential optical density of the saturate fraction.

9. The method of claim 8, wherein the shorter wavelength is 285 nanometers and the longer wavelength is 800 nanometers.

10. The method of claim 2, wherein determining the differential optical density of the aromatic fraction is accomplished by:
measuring an optical density of the aromatic fraction at a shorter wavelength and at a longer wavelength; and
subtracting the optical density of the aromatic fraction at the longer wavelength from the optical density of the aromatic fraction at the shorter wavelength to produce the differential optical density of the aromatic fraction.

11. The method of claim 10, wherein the shorter wavelength is 470 nanometers and the longer wavelength is 800 nanometers.

12. The method of claim 2, wherein determining the differential optical density of the resin fraction is accomplished by:
measuring an optical density of the resin fraction at a shorter wavelength and at a longer wavelength; and
subtracting the optical density of the resin fraction at the longer wavelength from the optical density of the resin fraction at the shorter wavelength to produce the differential optical density of the resin fraction.

13. The method of claim 12, wherein the shorter wavelength is 600 nanometers and the longer wavelength is 800 nanometers.

14. The method of claim 1, wherein the predetermined data includes correlations between optical density and exemplary saturate, aromatic, and resin fractions.

15. The method of claim 1, wherein correlating the optical density of each of the saturate, aromatic, and resin fractions to predetermined data to determine each of the saturate, aromatic, and resin fractions is accomplished by:
placing the predetermined data in memory of a computer;
inputting the optical density of each of the saturate, aromatic, and resin fractions to the computer; and
operating the computer to determine each of the saturate, aromatic, and resin fractions.

16. The method of claim 1, further comprising:
preparing the predetermined data, which is accomplished by:
separating a plurality of maltenes portions from a plurality of hydrocarbon fluid portions;
separating saturate, aromatic, and resin fractions from each of the plurality of maltenes portions;
determining an optical density of each of the saturate, aromatic, and resin fractions;
determining the weight percent of each of the saturate, aromatic, and resin fractions; and
correlating the optical density of each of the saturate, aromatic, and resin fractions to the weight percent of each of the saturate, aromatic, and resin fractions.

17. The method of claim 16, wherein the optical density of each of the saturate, aromatic, and resin fractions is a differential optical density.

18. The method of claim 16, wherein separating the plurality of maltenes portions from the plurality of hydrocarbon portions is accomplished by titrating each of the plurality of hydrocarbon fluid portions with heptane.

19. The method of claim 16, wherein separating the saturate, aromatic, and resin fractions from each of the plurality of maltenes portions is accomplished by:
introducing each of the maltenes portions to an activated alumina bed;
flushing the bed with heptane to separate the saturate fraction from the maltenes portion;
flushing the bed with toluene to separate the aromatic fraction from the maltenes portion; and
flushing the bed with dichloromethane/methanol to separate the resin fraction from the maltenes portion.

20. The method of claim 17, wherein determining the differential optical density of each of the saturate fractions is accomplished by:
measuring an optical density of each of the saturate fractions at a shorter wavelength and at a longer wavelength; and
for each of the saturate fractions, subtracting the optical density of the saturate fraction at the longer wavelength from the optical density of the saturate fraction at the shorter wavelength to produce the differential optical density of the saturate fraction.

21. The method of claim 20, wherein the shorter wavelength is 285 nanometers and the longer wavelength is 800 nanometers.

22. The method of claim 17, wherein determining the differential optical density of each of the aromatic fractions is accomplished by:
   measuring an optical density of each of the aromatic fractions at a shorter wavelength and at a longer wavelength; and
   for each of the aromatic fractions, subtracting the optical density of the aromatic fraction at the longer wavelength from the optical density of the aromatic fraction at the shorter wavelength to produce the differential optical density of the aromatic fraction.

23. The method of claim 22, wherein the shorter wavelength is 470 nanometers and the longer wavelength is 800 nanometers.

24. The method of claim 17, wherein determining the differential optical density of each of the resin fractions is accomplished by:
   measuring an optical density of each of the resin fractions at a shorter wavelength and at a longer wavelength; and
   for each of the resin fractions, subtracting the optical density of the resin fraction at the longer wavelength from the optical density of the resin fraction at the shorter wavelength to produce the differential optical density of the resin fraction.

25. The method of claim 24, wherein the shorter wavelength is 600 nanometers and the longer wavelength is 800 nanometers.

* * * * *